United States Patent [19]

Cover

[11] Patent Number: 4,571,534
[45] Date of Patent: Feb. 18, 1986

[54] ENERGY CONVERSION SYSTEM WITH FERMENTATION

[76] Inventor: John H. Cover, 24742 Via San Fernando, Mission Viejo, Calif. 92691

[21] Appl. No.: 542,062

[22] Filed: Oct. 14, 1983

Related U.S. Application Data

[63] Continuation-in-part of Ser. No. 457,627, Jan. 13, 1983, which is a continuation-in-part of Ser. No. 342,391, Jan. 25, 1982.

[51] Int. Cl.[4] .......................... G21D 7/02; H02K 44/00
[52] U.S. Cl. ......................................... 322/2 R; 310/11
[58] Field of Search ................... 322/2 R, 2 A, 11, 35, 322/47; 310/300, 306; 290/43, 54; 323/906; 204/129, 130

[56] References Cited

U.S. PATENT DOCUMENTS

| | | | |
|---|---|---|---|
| 3,375,664 | 4/1968 | Wells, Jr. | 290/1 R X |
| 3,443,129 | 5/1969 | Hammitt | 310/11 |
| 3,616,334 | 10/1971 | Aker et al. | 204/129 |
| 3,999,089 | 12/1976 | Barros | 310/11 |
| 4,191,901 | 3/1980 | Branover | 310/306 X |
| 4,381,462 | 4/1983 | Radebold | 310/11 |

OTHER PUBLICATIONS

Halacy, D. S., *The Coming Age of Solar Energy*, Pub. Avon Books, N.Y., 1973, p. 142.
Panati, Charles, *Break Throughs*, Pub. Berkley Books, N.Y., 7/1981, p. 296.

Primary Examiner—R. J. Hickey
Attorney, Agent, or Firm—Knobbe, Martens, Olson & Bear

[57] ABSTRACT

A system is disclosed for converting one form of energy into an alternate form of energy by means of a low-temperature process. A liquid flow loop with two vertical columns that are interconnected at the top and bottom circulates a fluid. A convective flow of this fluid is established by heating the fluid in one of the columns and cooling the fluid in the other column to establish a weight differential between the fluid in the two columns. An electric generator is placed on this loop so that, as the fluid flows through the loop and through the generator, electrical energy is generated. This electrical energy is used to electrolyze a second fluid, such as a solution of sulphuric acid, into gasses such as hydrogen and oxygen. The gasses so generated are used to increase the rate of flow of the fluid, and consequently the rate of electric energy production. The preferred embodiments incorporate a fermentation process to produce Carbon dioxide gas and heat energy. In one embodiment, these gasses are injected into the rising column of the fluid to increase the weight differential between the fluid in the two columns and enhance the convective flow of that fluid. These gasses, which contain chemical energy, are then removed from the loop at the top of this column. Alternatively, the gasses can be accumulated at high pressure, and the pressure used to inject a volatile fluid into the loop.

29 Claims, 15 Drawing Figures

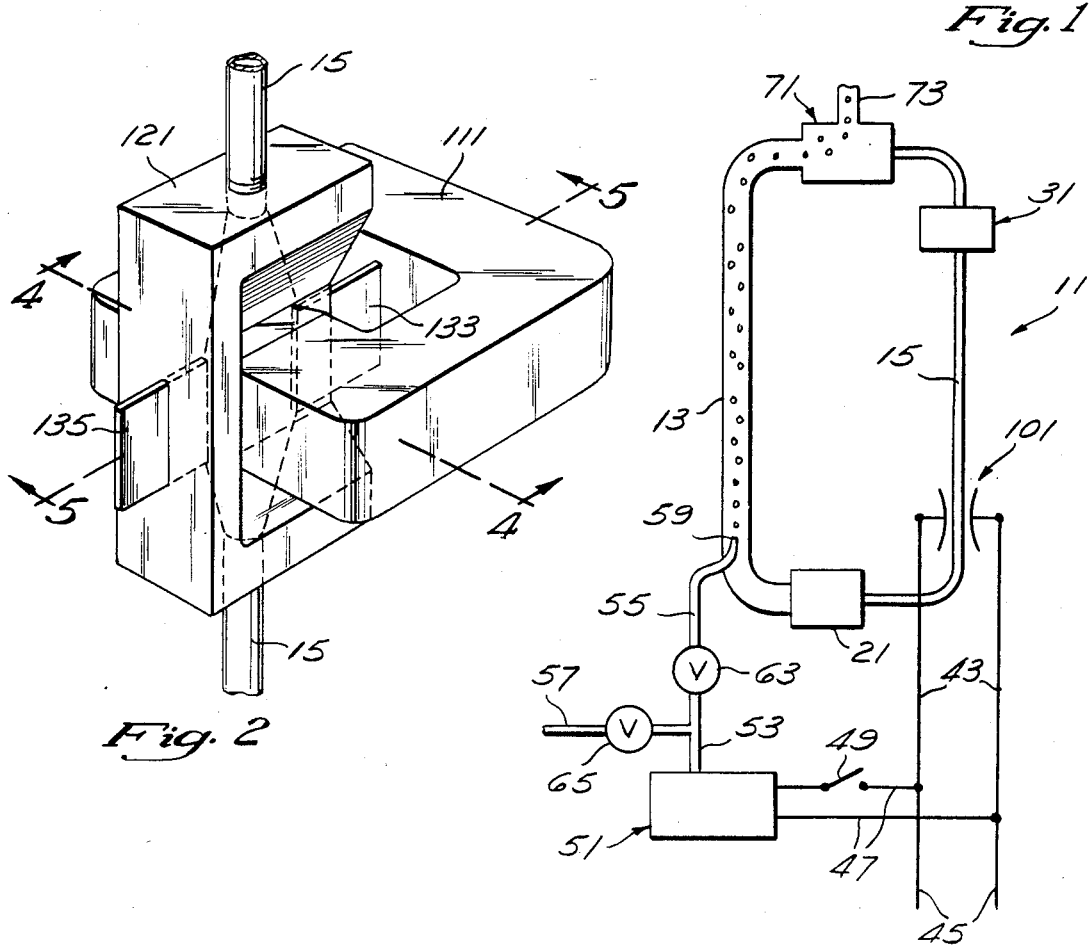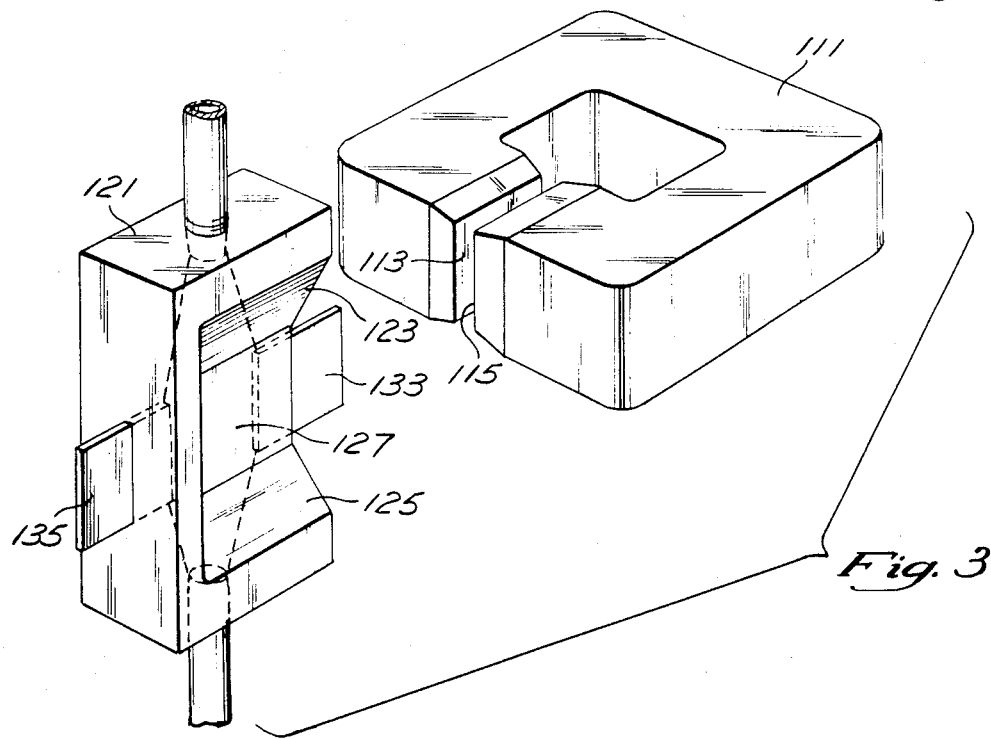

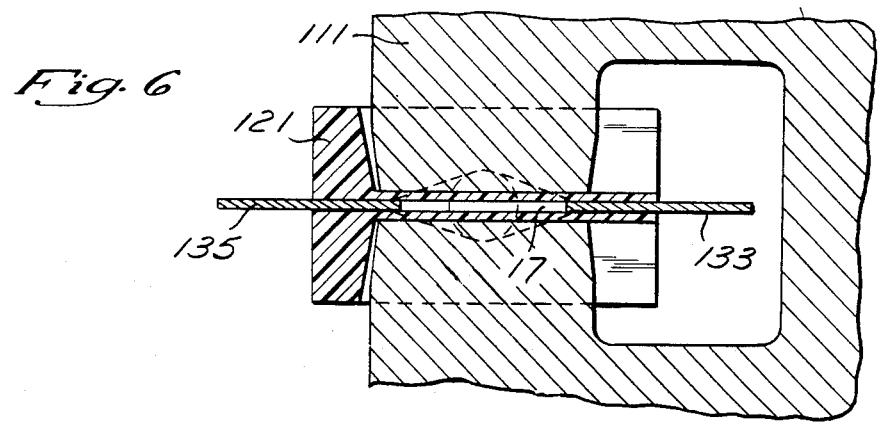
Fig. 6
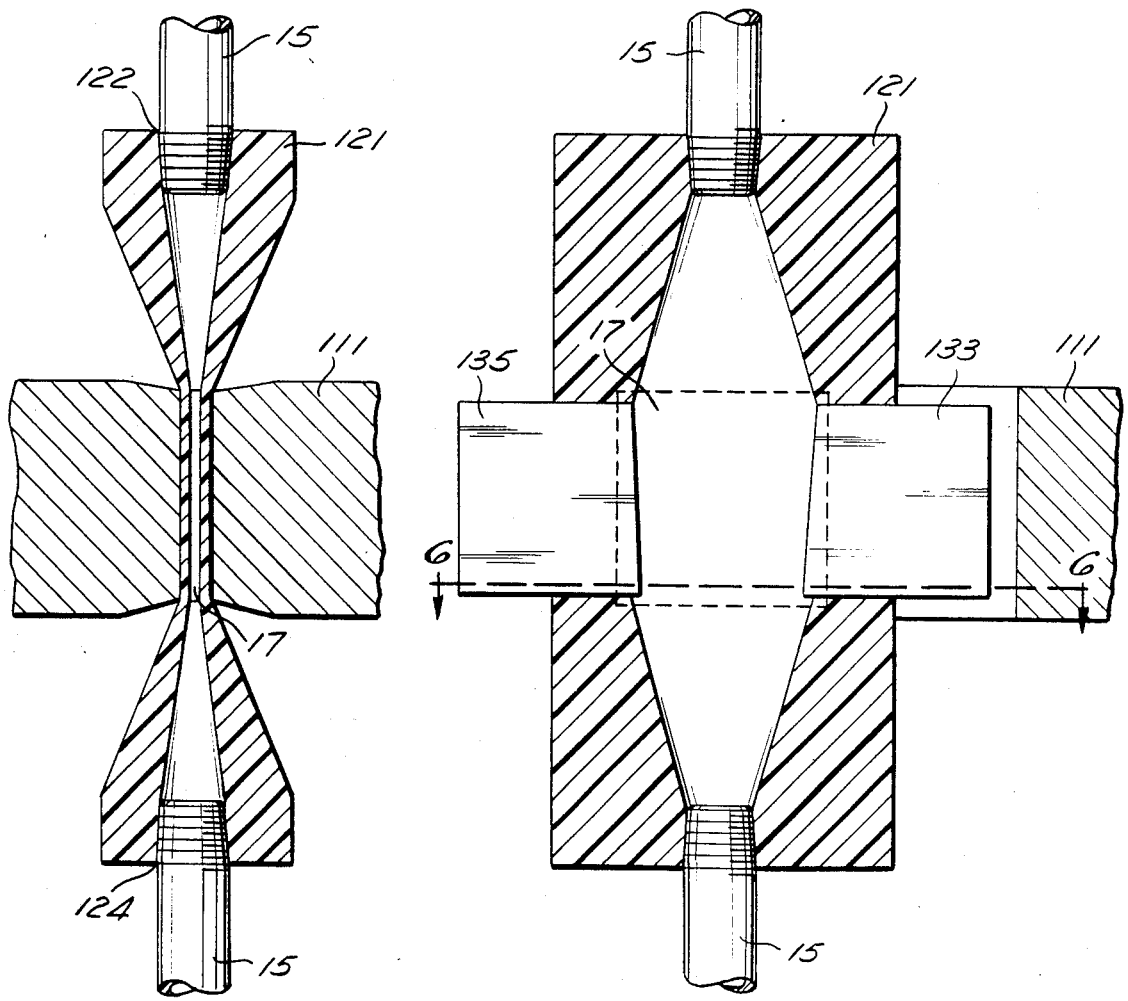
Fig. 4
Fig. 5

ENERGY CONVERSION SYSTEM WITH FERMENTATION

RELATED APPLICATIONS

This application is a continuation-in-part of application Ser. No. 457,627, filed Jan. 13, 1983, and entitled "Energy Conversion System", which in turn is a continuation-in-part of application Ser. No. 342,391, filed Jan. 25, 1982, and entitled "Thermal Energy Conversion."

BACKGROUND OF THE INVENTION

With the advent of higher prices for the energy the world consumes, much interest has been generated in new sources of energy and in more efficient uses of this energy. One of the energy conversion devices for which promise has been held is the magnetohydrodynamic generator (MHD). The basis for the operation of an MHD is that passing an electrically conducting fluid through a strong magnetic field will produce an electric potential between opposite sides of the throat through which the conducting fluid flows. The magnitude of the power generated with a given fluid is proportional to the velocity of the fluid through the throat.

MHD development has typically focused on the use of high temperature, high pressure gas or plasma, although some systems have been developed using an electrically conducting liquid. The temperature of the plasma or liquid used in these devices is usually on the order of several hundred to a few thousand degrees Celsius. The pressure under which the working fluid operates is also very high in most systems, on the order of several hundred to a few thousand pounds per square inch. The use of such high temperature and pressure fluids limits the choice of materials out of which the system can be made. The high temperatures and high pressures in these systems also make the systems prone to leaks and contribute to the rapid deterioration of machinery such as pumps used in the system.

To provide the flow of conducting fluid through the MHD throat, some systems have incorporated means for establishing a convective flow of the fluid around a closed loop. This convective flow is established by heating the fluid at one point in the loop and cooling it at another. Such a system is shown in U.S. Pat. No. 3,375,664 to Wells. It has been found, though, that the low velocity thus obtained has not been sufficient to permit the MHD to generate more than a few milliwatts of power even with vertical leg members up to 100 feet tall. Another means of causing a flow of the conducting fluid through an MHD loop has been to establish a convective flow by introducing a gas into part of the loop to create a density differential between the fluid in different sections of the loop. This has typically been accomplished by boiling either the conducting liquid or a second fluid and using the vapor bubbles to leviate one column of the fluid. A system that operates in this manner is disclosed in U.S. Pat. No. 3,443,129 to Hammitt. Such systems, however, have been troublesome, since boiling the fluid takes thermal energy from the system, reducing the heat in the conducting fluid in the rising column. Also, the height and temperature of the rising column are severely constrained by the need to prevent condensation of the gas bubbles before they reach the top of the column.

Another energy conversion method, which is well known in the art, is the fermentation process, which converts glucose into ethyl alcohol and Carbon dioxide in the presence of yeast produced enzymes. The fermentation process gives off heat energy. The ethyl alcohol is a convenient form for storing chemical energy. However, state of the art fermentation systems are relatively inefficient. The Carbon dioxide gas, which is a product of fermentation, is merely released into the atmosphere thereby wasting any energy which could be exploited from the fermentation gas formation. Additionally, the heat given off by fermentation is removed using conventional refrigeration systems which require the use of external energy making the fermentation process even less efficient.

SUMMARY OF THE INVENTION

The present invention includes an apparatus for converting one form of energy into an alternate form of energy, and comprises a fluid conduit through which flows a fluid, a first means for establishing a flow of said fluid through the fluid conduit, an electric generator coupled to the conduit to generate electric energy from the flowing fluid, a gas generator that uses a portion of the electric energy generated by the electric generator to form a gas, and an apparatus that uses at least a portion of these gases to increase the rate of flow of the fluid through the conduit.

The present invention efficiently converts thermal energy (heat) into an alternate form of energy by means of a low-temperature process. The invention consists of a fluid flow loop with two vertical columns interconnected at the top and the bottom. The fluid that flows in this loop is an electrically conducting fluid, preferably a liquid such as mercury. The column in which the fluid rises is heated to a temperature of approximately 40°–150° C. by a thermal source and the column in which the fluid flows down is cooled to a temperature of approximately 0°–30° C. by means of a lower temperature heat sink. The difference in the density of the fluid in these columns induces a convective flow of that fluid through the loop. An MHD is coupled to one of these vertical columns. The MHD includes a magnet that creates a strong magnetic field perpendicular to the flow of the fluid. As the fluid flows through throat sections that have electrodes in contact with the fluid, an electric potential is generated between the electrodes, causing an electric current to flow through the electrodes and through an external electric circuit, from which power may be drawn. The key to the present invention is that the electric power so produced is largely fed back to augment, or speed up, the flow of the conducting liquid. This is accomplished by using the electric power to dissociate water molecules in an electrolytic solution, such as sulfuric acid, $H_2SO_4$, and inject some or all of the gasses obtained ($H_2$ and $O_2$) into the rising column of conducting liquid. The gas is removed from the loop at the top of the rising column and may be put to any of a number of uses.

The remainder of the gasses, which are not injected into the loop may be taken directly from the electrolysis and put to use. Among the possible uses for the gasses produced by this system are burning to produce heat, power and pure water using them to synthesize other fuels, such as methane, methanol. The introduction of the gas into the rising column greatly reduces the density and weight of the rising column of electrically conducting liquid, and hence increases the weight difference between the two columns of liquid. As the weight difference between the columns is increased, the convective flow of the liquid is increased, further increasing the production of electrical energy. With the increased electrical output, more gasses are produced, and the convective flow velocity of the liquid is further increased, which additionally increases the amount of electric power generated by the MHD. The rate of generation of the electrolyzed gasses is increased until an equilibrium is established between the generation of the gasses and the viscous and other flow retarding forces.

Another key feature is that the present invention incorporates a fermentation process which, as a by-product, produces Carbon dioxide gas. The fermentation process further produces the gas at high pressure. At least a portion of this fermentation gas is additionally used in similar fashion to the use of the electrolysis gasses to cause a flow of the conducting liquid.

The Thermal Energy Conversion and Fermentation System of the present invention has numerous advantages over the MHD systems previously developed. These advantages include:

(1) lower operating temperatures for the working fluid;
(2) lower pressures in the system loop;
(3) less severe constraints on the design and size of the system components;
(4) less severe constraints on the choice of materials out of which the system components are made;
(5) greater power output with a smaller system due to increased operating efficiency; and
(6) more efficient use of fermentation process.

BRIEF DESCRIPTION OF THE DRAWINGS

FIG. 1 is a schematic drawing of the Thermal Energy Conversion System incorporating the present invention.

FIG. 2 is a perspective view of the magnetohydrodynamic generator coupled to the fluid flow loop.

FIG. 3 is a perspective view of the magnetohydrodynamic generator with the magnet withdrawn from the throat section of the fluid flow loop.

FIG. 4 is a cross-sectional view of the magnetohydrodynamic generator used in the present invention taken along lines 4—4 of FIG. 2.

FIG. 5 is a cross-sectional view taken along line 5—5 of FIG. 2.

FIG. 6 is a cross-sectional view taken along line 6—6 of FIG. 2.

DESCRIPTION OF THE PREFERRED EMBODIMENT

General System

Figure 7:
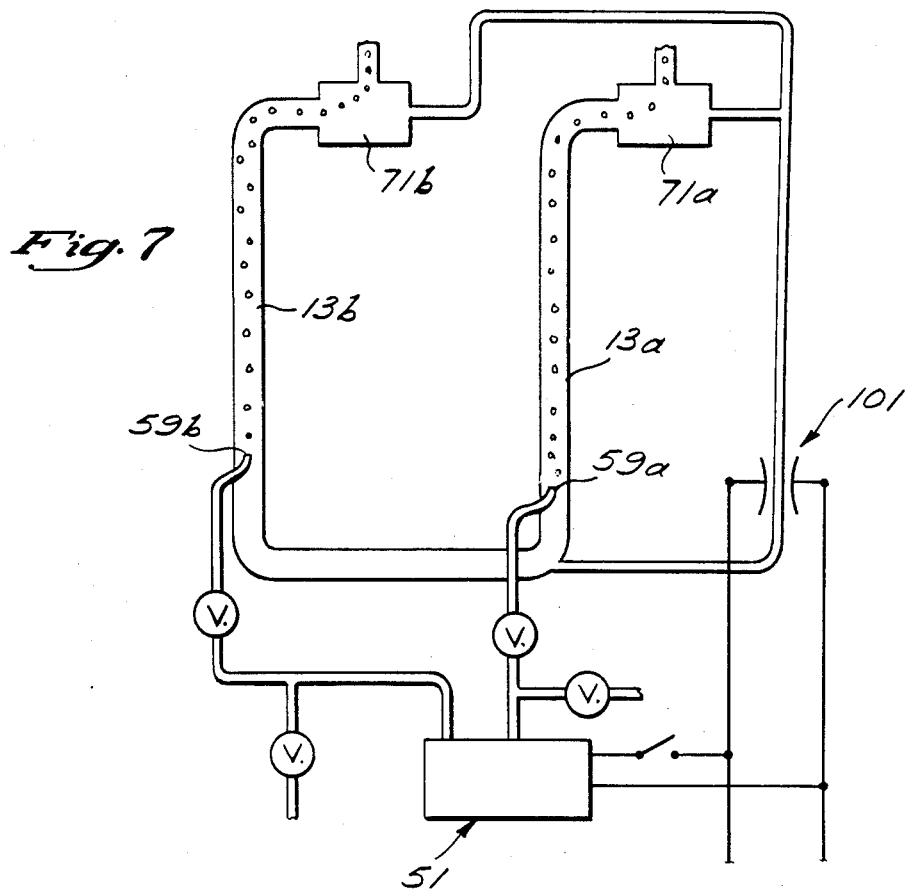
FIG. 7 is a schematic drawing of a first alternative embodiment of the Thermal Energy Conversion System.

The system of the present invention is shown schematically in FIG. 1. It comprises a fluid loop 11 that is preferably closed, including first and second vertical columns or legs 13 and 15 that are interconnected at the top and bottom. A conducting fluid, such as liquid mercury, flows through the loop 11. Liquid mercury is advantageous because of its high electrical conductivity, high density, and low specific heat value, but other electrically conductive fluids such as electrolytic solutions may also be used, depending on cost considerations, equipment design or availability, or other factors. On the second column 15 is an electric generator 101, such as a magnetohydrodynamic generator (MHD) 101. Electrical leads 43 transmit the electric potential generated by the MHD 101.

A source of thermal energy 21 is coupled to the loop near the bottom of the first column 13. This source 21 may be virtually any type of thermal energy source, including a burner for fossil fuels or a heat exchanger drawing heat from a reservoir heated by either solar energy or geothermal energy. The temperature increase provided by the thermal energy source 21 depends upon the environment in which the system operates. This temperature increase can range from 20° to 100° C. or more, and is preferably at least 40° C.

A heat exchanger or other device for removing thermal energy from the working fluid 31 is connected to the loop near the top of the second column 15 to draw heat from the conducting fluid and transfer it to a heat sink, such as a large body of cool water that is isolated from the sun, or some other low temperature body, which may be a body of ice if the system is used in a particularly cold environment.

A gas injector 59 for introducing gas into the system loop is placed near the bottom of the first column 13. Gas injector 59 is a gas nozzle outlet of conventional design and is substantially centrally located in column 13.

A gas separator 71 is coupled to the loop near the top of the first leg 13. Separator 71 may be of conventional design for drawing gas from a two-phase flow. Gas separator 71 permits the liquid mercury to continue flowing around the loop, while removing the gasses introduced by gas injector 59 to be drawn off through outlet 73. Outlet 73 is connected so that the gasses may be put to other uses, such as burned to produce heat or power, stored to be burned later, or used to synthesize other fuels, such as methane or methanol.

An electrolytic gas generator 51 uses the electrical energy generated by the MHD 101 to electrolyze an electrolyte, such as a solution of sulfuric acid ($H_2SO_4$) to generate hydrogen and oxygen gas, which contain chemical energy. The pressure at which the gas generator must be capable of producing the gasses depends upon the static pressure in column 13 at gas injector 59 caused by the column of mercury, since, to enter the column, the gas must be at a pressure at least as great as that of that static pressure. This static pressure depends on the height of the columns 13 and 15. For a small system with short columns, the gas generator 51 need only produce the gas at a pressure of a few pounds per square inch, while a gas generator coupled to a system using much taller columns needs to produce the gas at a pressure on the order of a few hundred pounds per square inch.

Outlet 53 from the gas generator 51 is preferably designed to keep the oxygen and hydrogen formed by the gas generator separate, since together they form a potentially explosive mixture. Outlet 53 branches into pipes 55 and 57. Pipe 55 leads to gas injector 59, so that part or all of the gasses generated by the electrolytic gas generator 51 may be injected into the first column 13. Valve 63 is provided on pipe 55 to control the volume of gas entering the fluid flow loop. Pipe 57 leads to a device for either storing or using the gasses. Advantageously, pipe 57 also keeps the gasses segregated, so that some of whichever of the gasses is injected into the column 13 may, if desired, also be diverted away from the flow loop, and stored or used directly. Valve 65 on pipe 57 controls the volume of gas being diverted away from the flow loop. Adjusting the valves 63 and 65 permits careful control of the portion of gasses that goes directly to other uses and the portion introduced into the fluid flow loop.

Electrical leads 43 and 47 permit the power generated by the MHD 101 to be transferred to the electrolytic gas generator 51. This feedback of the power generated back into the system greatly increases the system's efficiency. Leads 45 permit power that is not used to operate the gas generator 51 to be drawn off the system and used for other purposes.

The MHD

The MHD 101, shown in FIGS. 2-6, includes a magnet 111 with closely juxtaposed north and south poles 115 and 113, a nonferromagnetic shock 121, and electrodes 133 and 135. Between the poles 115 and 113 is a throat section 17 of the block 121 (FIG. 4). This throat section 17 is defined by two closely juxtaposed rectangular walls 127 and 129 to allow a thin sheet of the mercury to pass between the poles of the magnet. The magnetic poles 113 and 115 are closely juxtaposed to maximize the intensity of the magnetic field across the sheet of mercury passing through throat section 17. Block 121 further includes threaded openings 122 and 124 for receiving the ends of the tubular piping that forms the remainder of the second column 15. The passage through which the mercury passes is tapered within the portions of the block 121 above and below the throat section 17 to form a transition between the tubular section of the second leg 15 and the thin throat section 17. As shown in FIG. 2, the exterior of the block 121 is also narrowed at throat section 17 so it will fit between the poles 113 and 115 of the magnet 111.

Electrodes 133 and 135 (FIG. 5) are placed on either side of this throat section 17 to tap the electric potential created between these two sides of the throat section. These electrodes are advantageously shaped so that continuous contact between the electrodes and the mercury flowing through the throat section 17 is promoted.

The throat section 17 is sized so that a venturi effect provides a ratio of approximately five to one between the speed of the mercury through the throat and the speed through the other sections of the loop.

The fluid flow passage through the MHD 101 must be constructed to contain the mercury flowing through it, particularly at the threaded openings 122 and 124, and at the points at which electrodes 133 and 135 enter throat section 17. But the passage is not subjected to the very high pressures that the MHD throat sections of systems that use a plasma as the working fluid must contain.

The Electrolytic Gas Generator

Electrolysis occurs when an electric current is passed through an electrolyte between two electrodes, an anode and a cathode. Ions in the solution move to and from the anode and cathode so that material may be transported and deposited on one of the electrodes, new compounds may be formed, or gasses may be liberated. Certain electrolytes, such as sulfuric acid, sodium hydroxide, and potassium carbonate, when dissolved in water, cause the water itself to decompose into its component parts, hydrogen and oxygen, when a current is passed through the solution.

The amount of material or gas formed by the electrolysis can be found using Faraday's Laws, which say that (1) the amount of chemical change produced by an electric current is proportional to the quantity of electricity and (2) the amount of different substances liberated by a given quantity of electricity are proportional to their chemical equivalent weights. (Equivalent weight=atomic weight divided by valence change.) Thus, the amount of material or gas produced is proportional to the current passed through the solution. When water is electrolyzed, the volume of hydrogen and oxygen produced is proportional to the current passed through the solution.

An example of a simple electrolytic gas generator that may be installed in the present system as gas generator 51 is a fully charged automobile storage battery comprising lead plates immersed in a solution of sulfuric acid. As current is passed through the solution in the cell the water in the solution is dissociated into hydrogen and oxygen. The hydrogen is given off at one of the electrodes, and the oxygen at the other. As the electrolyte solution is dissociated into its component parts to form the gasses, the water must be replaced, but the acid itself remains in the solution.

The gasses produced should be kept separate, since, in the case of hydrogen and oxygen, the two gasses together form an explosive mixture. This separation can be maintained by placing a membrane between the electrodes.

Since the amount of gas produced is proportional to the current, but not the pressure under which the cell operates (except at the extremes), the gasses may be produced at relatively high pressures with negligible increases in the power consumed. Generation of gasses at a presume of forty atmospheres is possible with electrolysis. Even by conservative estimates, the electrolytic process can produce high pressures is gasses 15% more efficiently than standard mechanical pumps.

Other types of electrolytic cells may also be used as gas generator 51. A cell comprising a nickle anode and iron cathode immersed in a solution of sodium hydroxide in water produces oxygen at the anode and hydrogen at the cathodes. Nickel electrodes immersed in a solution of potassium carbonate may also be used to produce hydrogen and oxygen.

The Thermal Energy Source

The thermal energy source 21 may be one of a number of available apparatuses for transferring thermal energy to the fluid circulating in the loop. The purpose of the thermal energy source 21 is to increase the temperature of the liquid in column 13 relative to the liquid in column 15 so that a density differential is established between the mercury in the two columns, causing a convective flow of the fluid liquid around the loop. Thus, the greater the temperature differential that can be established, the greater the convective flow of the liquid.

Particularly appropriate as a thermal energy source, in light of the interest in renewable resources, is a heat exchanger drawing heat from a solar heated reservoir. Panels for heating liquids such as water using solar energy are commercially available in many sizes from numerous sources, as are containers for storing the solar heated water. Heat exchangers are also readily available that can be coupled to the closed loop and are suitable for circulating the heated water from the reservoir and transferring its heat to the mercury circulating in the closed loop. Such apparatus can provide a 40° C. temperature differential, which is suitable for operation of the system.

Also appropriate would be the use of a heat exchanger circulating geothermally heated water. Geothermally heated water often is at a much higher temperature than solar heated water would be, on the order of 120°-180° C., and thus would be able to produce a greater temperature differential between the mercury in column 13 and the mercury in column 15. This increased temperature differential is advantageous in that the density differential between the mercury in the two columns is greater, and consequently the convective flow of the mercury is increased. But, the availability of geothermal energy is limited.

In addition to the sources of thermal energy just discussed, a fossil fuel burner of conventional design may be used as thermal energy source 21 to directly heat the circulating mercury.

Since the important consideration for operation of the system is the temperature differential between the liquid in the two columns 13 and 15, heat exchanger 31 must be connected to a heat sink capable of absorbing from the liquid the heat transferred to it by thermal energy source 21. In a system located in a temperature climate, this is most effectively done by circulating in the heat exchanger cool water drawn from a large reservoir kept cool by isolating it from exposure to the sun. In a colder climate, a large body of ice may be used, which would permit the temperature of the mercury to be reduced to 0° C., or perhaps lower.

Alternatives for Energy Input

The thermal energy source 21 inputs energy into the system to create the flow of fluid through the conduit to allow the electrical generator 101 to produce electrical energy. Thus, the thermal energy source 21 can be replaced by any of a number of other mechanisms for inputting energy to the fluid, such as a pump that impacts kinetic energy directly to the fluid.

The flow creator 21 begins the movement of fluid around the loop and through the electric generator 101 so that the production of electric energy is begun. Once the production of electric energy has begun, the gas generator 51 can be used to produce gas, and the gas can be used by the flow augmentation means to increase the rate of flow, and consequently increase the rate of production of electric energy. The input of energy through the energy source 21 continues to ensure the continued flow of fluid through the conduit.

If the flow creator 21 is a pump or other non-thermal energy source, then obviously the heat sink 31 is not necessary at the top of the second column 15, since there is no additional heat in the working fluid that must be removed.

Operation of the System

In operation, thermal energy is added by heat source 21 to the conducting fluid in the first column 13 to lower the density of the fluid in that column, thereby inducing a convective flow of the mercury. The heat so introduced into the conducting fluid is removed by the heat exchanger 31 at the top of the second column 15 to ensure the continuation of the temperature differential (and the density differential) between the mercury in the first and second columns. As the fluid flows downward in the second column, it flows through the throat section 17 of the MHD 101 in a direction perpendicular to the magnetic field established by the magnet 111. This flow, by reason of Faraday's Laws, creates an electric potential between the sides of the throat section 17, which is tapped by the electrodes 133 and 135. This purely temperature-induced convective flow through the MHD will generate a very low power output. The power output is low due to the low velocity of the electrically conducting fluid through the MHD.

The electric potential is produced in the following manner: When a sheet of conducting material, e.g., mercury, is passed through a magnetic field that is perpendicular to the direction in which the conducting material is moving, an electric potential develops between points on the sheet of conductive material that lie on an axis perpendicular to both the direction of movement of the conductive sheet and the direction of the magnetic field.

As the conductive fluid flows with velocity v through the perpendicular magnetic field B, a force is exerted on each charge carrier in a third, mutually perpendicular direction. This force F is given by the vector equation:

$$F = qv \times B$$

in which q is the charge of each charge carrier. The electric field intensity (E) resulting from this force is given by the vector equation:

$$\underline{E} = \frac{F}{q} = \underline{v} \times \underline{B}.$$

This electric field yields an electric potential between two sides of the channel through which the conductor flows. This potential is:

$$E = \int E \cdot dL = \int (v \times B) \cdot dL$$

in which L represents the width of the sheet of conductive fluid.

In the MHD loop, flow equilibrium is reached when the electromotive force so generated equals the force driving the fluid flow, the difference in the weight of the mercury in the two columns.

By using the electric power generated by the MHD 101 to electrolyze a second fluid in gas generator 51 and introduce the gasses so generated into the rising first column 13, the efficiency of the system can be greatly increased due to the increased rate of flow of the electrically conducting fluid through the MHD. When the gasses produced by the electrolytic gas generator 51 are introduced into the first column 13, the density and weight of the mercury in that column is substantially decreased, which increases the density and weight differentials between the fluid in the first column 13 and the fluid in the second column 15. This increased differential greatly enhances the convective flow of the mercury around the loop, increasing the rate of flow of the conducting fluid through the throat 17 of the MHD section of the loop. As this flow through the throat section is increased, so is the power produced by the MHD. This increase continues until a new flow equilibrium is reached. The gas injected into the upflow column 13 also contains mechanical energy, because it is under pressure. When the gas in injected, it occupies a small volume because of the high pressure at which the gas generator 51 creates it. As the gas bubbles rise in the column 13, the pressure of the surrounding fluid decreases, allowing the gas to expand. It has been found that the energy of compression of the gas is converted into kinetic energy of the working fluid as the expanding gas works on the fluid.

The gasses introduced into the loop, which also contain chemical energy, are separated from the conducting fluid at the top of the loop by the gas separator 71 and may be put to any of a number of uses, as mentioned above.

Each cycle of flow (once around the loop) extracts an amount of energy proportional to the weight difference between the two columns (represented by the equation $E = dW \times h$, in which dW is the difference in weight and h is the height of the column). The amount of power that can be obtained from the system depends upon the speed or time it takes to complete the stroke, i.e., the rate at which the work is done. Thus, the power is given by the equation $P = dW \times v$, in which v is the speed of the fluid flow.

As the system continues to operate, the MHD 101 may generate more power than is needed to operate the electrolytic gas generator 51. When this occurs, electrical leads 45 may be attached to an external load suitable for using this excess power. Alternately, electrical leads 45 may be connected to a battery to store the power for later use. Accordingly, the system may be advantageously used to convert the thermal energy supplied by thermal energy source 21 to both chemical energy in the form of gasses and electrical energy.

ALTERNATIVE EMBODIMENTS

General System

Alternatively to using a single upflowing column 13 in the MHD loop 11, two or more columns 13a and 13b may be used, as shown in FIG. 7. In this embodiment, one of the gasses produced by electrolytic gas generator 51, for example the oxygen may be injected into column 13a and the other gas, the hydrogen, may be injected into column 13b. In this way, both the gasses produced may be used to supplement the convective flow, while keeping the gasses separate. Since both gasses produced by the gas generator are used, the utility of the feedback of the electrical energy generated by the MHD 101 is enhanced. This embodiment requires at least two gas separators 71a and 71b (one to separate each gas out of the flow), and a gas injector 59a and 59b for each column 13a and 13b.

The Electrolytic Gas Generator

Figure 8:
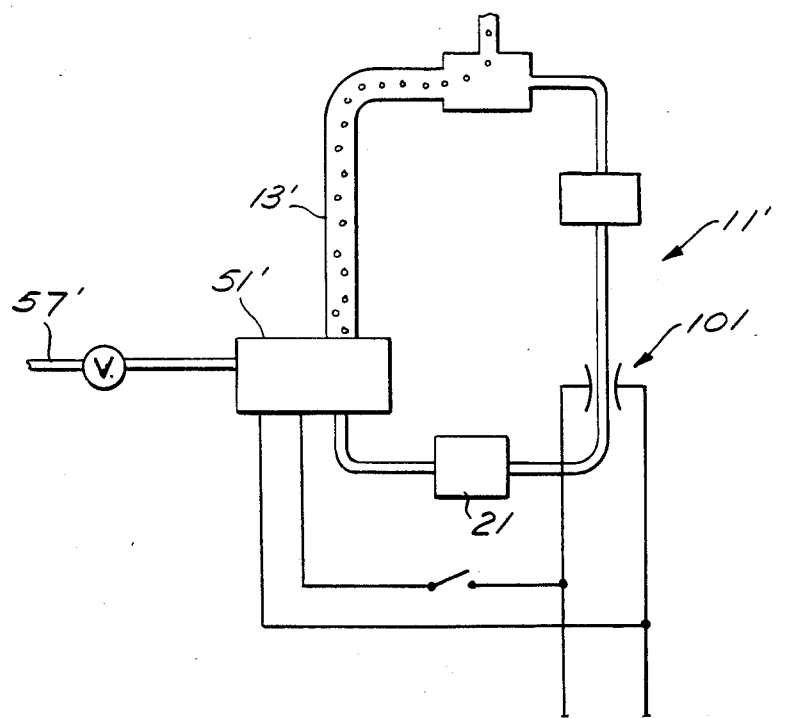
FIG. 8 is a schematic drawing of a second alternative embodiment of the Thermal Energy Conversion System.

As an alternative to using a liquid metal such as mercury in the MHD loop 11 and electrolyzing a separate electrolyte in gas generator 51, a electrolyte may be circulated through the MED loop 11' (FIG. 8) and passed through electrolytic gas generator 51' so that the MHD working fluid itself is electrolyzed. From gas generator 51' part or all of the gasses may be injected into the column 13'. Pipe 57' allows whatever of the gasses are not injected into column 13' to be diverted and put directly to use.

Alternative Electrical Generator 101

Figure 9:
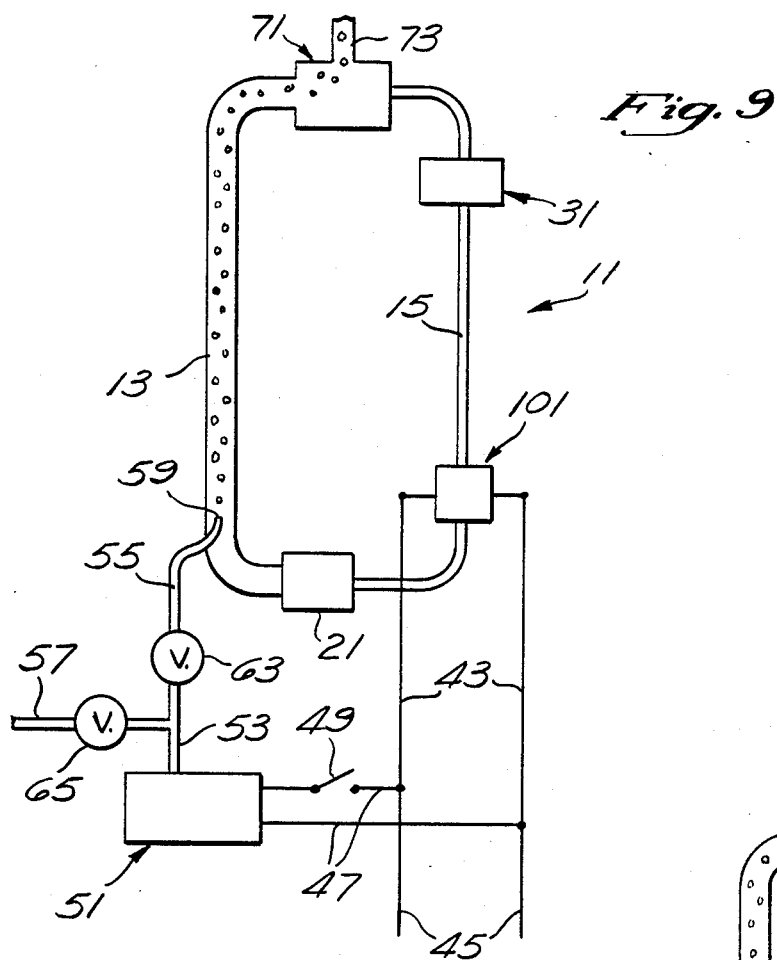
FIG. 9 is a schematic drawing of a third alternative embodiment of the Energy Conversion System.

As an alternative magnetohydrodynamic generator as the electric generator 101, any of a number of electric generators that generate electrical energy from a moving fluid can be used. FIG. 9 is a schematic drawing of the system with a general designation for the electrical generator 101. For example, the electrical generator 101 can be a homopolar or Faraday Disk type of generator. Another example of such an alternative electric generator is a common turbine generator, in which the moving fluid turns the blades of the turbine to generate electrical energy in a known fashion. FIG. 9 shows the system of FIG. 1 with a more general representation of the electric generator 101.

It would be apparent to those skilled in this art of electrical energy generation that any type of generator that converts the kinetic energy of a moving fluid to electric energy can be used as the means for generating electric energy from the moving fluid.

First Alternative Flow Augmentation Means

Figure 10:
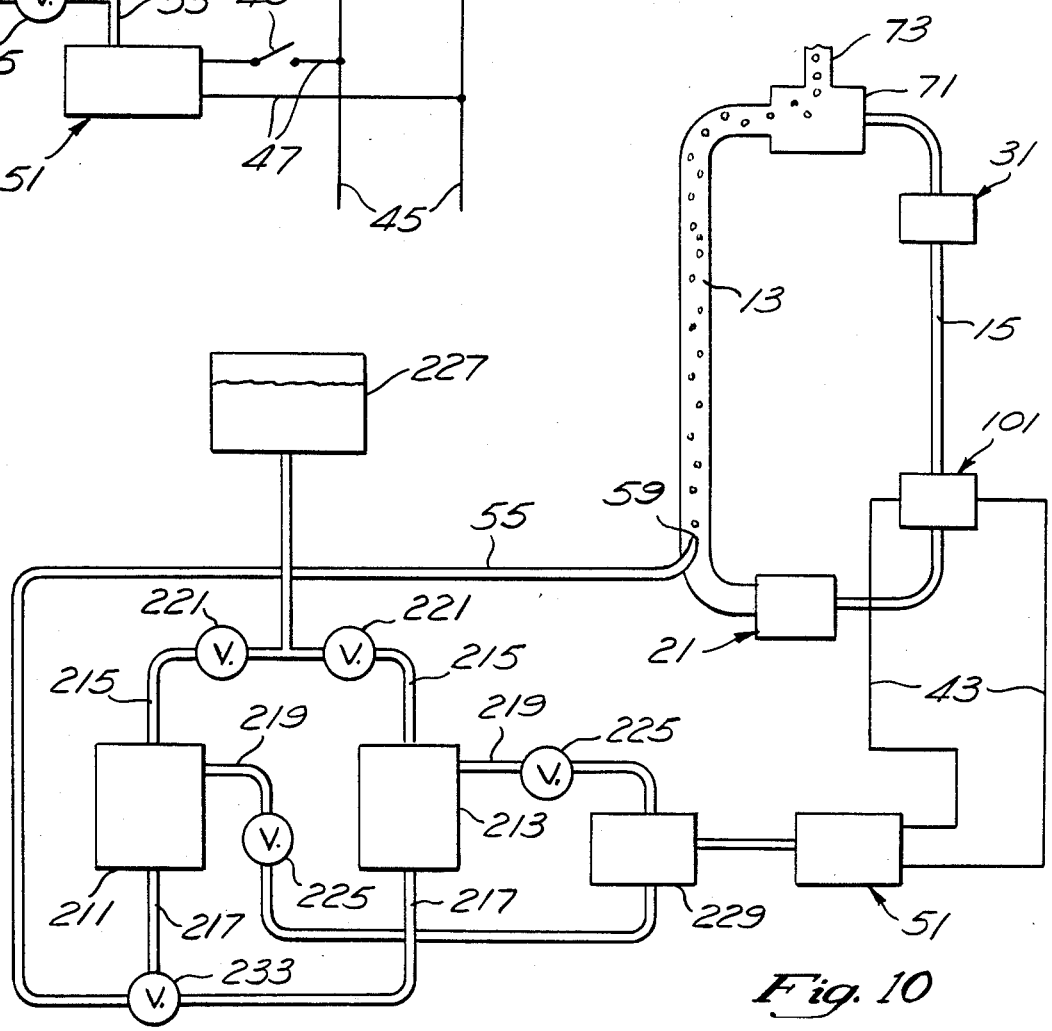
FIG. 10 is a schematic drawing of a fourth alternative embodiment of the Energy Conversion System.

Referring now to the embodiment of the system of the invention shown in FIG. 10, the overall system is roughly the same as that described above, with a pair of substantially vertical flow conduits 13,15, an electric generator 101, and a gas generator 51 that uses the electric energy generated by the electric generator 101. The gas generator 51 and the electric generator 101 are connected by the electrical leads 43. The system again includes an energy input means 21, such as a thermal energy source or other means to begin the flow of fluid through the conduit, such as a pump.

Rather than injecting the gasses developed by the electrolytic gas generator 51 directly into the working fluid in the upflow column 13, the system of this alternative embodiment uses the gasses generated by the electrolytic gas generator 51 to pressurize a volatile fluid, which is then injected into the upflow tube 13, where it changes to its gas form and reduces the density of the working fluid to further increase the rate of flow of the working fluid through the conduit.

A pair of fluid containers 211,213 each have fluid inlets 215, fluid outlets 217, and gas inlets 219. Each of these inlets 215,219 and outlets 217 is controlled by a valve 221, 233, 225 to control the flow of fluid into and out of the container 211, 213.

The gas from the gas generator 51 is alternately supplied to the first and second fluid containers 211,213. Initially, the fluid inlet valve 221 on the first fluid container 211 is opened and the first container is substantially filled with the volatile fluid from the reservoir 227. This volatile fluid readily changes from the liquid phase to the gas phase at relatively low temperatures, on the order of the temperature of the working fluid in the conduit loop. When the volatile fluid enters the first container 211, it is in the liquid phase. After the first container 211 has been substantially filled with the fluid, the fluid inlet valve 221 is closed, and the gas inlet valve 225 is opened. The gas is supplied from the gas generator 51 to the gas inlet 219 at a high pressure, so the gas builds the pressure inside the container 211. When the pressure reaches a specified level, the fluid outlet valve 233 is opened, and the pressure inside the fluid container 211 drives the volatile fluid out of the first fluid container 211 through the injection conduit 55 and into the injection nozzle 59. The injection nozzle 59 is similar to the injection nozzle 59 of the embodiment shown in FIG. 1 and described above.

As the volatile fluid is injected into the upflow column of the fluid conduit 13, the fluid is transformed to its gas phase by the heat of the working fluid that surrounds the injection nozzle 59. As the volatile fluid is at a very high pressure as it enters the upflow tube 13 of the conduit, the gas bubbles it forms are rather small. As the gas bubbles move up in the column with the upflowing fluid, these bubbles expand in size as the external pressure on them is less in the column 13 than it was in the injection conduit 55. These expanding bubbles further increase the flow of the working fluids through the conduit.

While the first fluid container 211 is being pressurized, the fluid inlet valve 221 for the second fluid container 213 is opened and the volatile fluid is allowed to flow into the second fluid container 213 to substantially fill it. The second fluid container 213 is then pressurized in the same way as first fluid container 211 while the volatile fluid is being driven out of the first fluid container 211.

While the second fluid container 213 is being pressurized, the first container 211 is again filled with the volatile fluid. As the volatile fluid is driven from the second fluid container 213, the first container 211 is again pressurized. This alternating process continues indefinitely, using the two fluid containers 211,213 to maintain a constant flow of volatile fluid through the injection conduit 55 at a high pressure. A mixer 233 where the two outlets 217 from the fluid containers 211,213 join ensures that the flow from the containers is properly alternated.

Obviously, more than two of the fluid containers 211,213 may be used in a system that operates such as this to further increase the supply of the volatile fluid to the conduit.

To minimize the need for pumps and other expensive equipment, the fluid containers 211, 213 are fed from the reservoir 227 that is at an elevation higher than the elevation of the fluid containers 211, 213. In this way, when the fluid inlet valve 221 on one of the fluid contains 211, 213 is open, the fluid will flow into the container by gravitational force, eliminating the need for a pump or other fluid moving apparatus to fill the containers.

To ensure an adequate high pressure supply of gas to pressurize the fluid containers 211, 213, a gas accumulator 229 is connected to the output of the gas generator 51. This accumulator 229 collects the gas generated by the gas generator 51 and allows the gas to build up to a very high pressure. It is well known that the electrolysis process of gas generation can produce gasses at very high pressures without significant loss in efficiency or overall energy consumption. Thus, the gas accumulator 229 allows the pressure of gas to be built up before it is fed through the gas inlets 219 to the first and second fluid containers 211, 213.

The gas separator 71 at the top of the upflow column 13 allows the gaseous volatile fluid to be removed from the conduit loop.

Second Alternative Flow Augmentation Means

Figure 11:
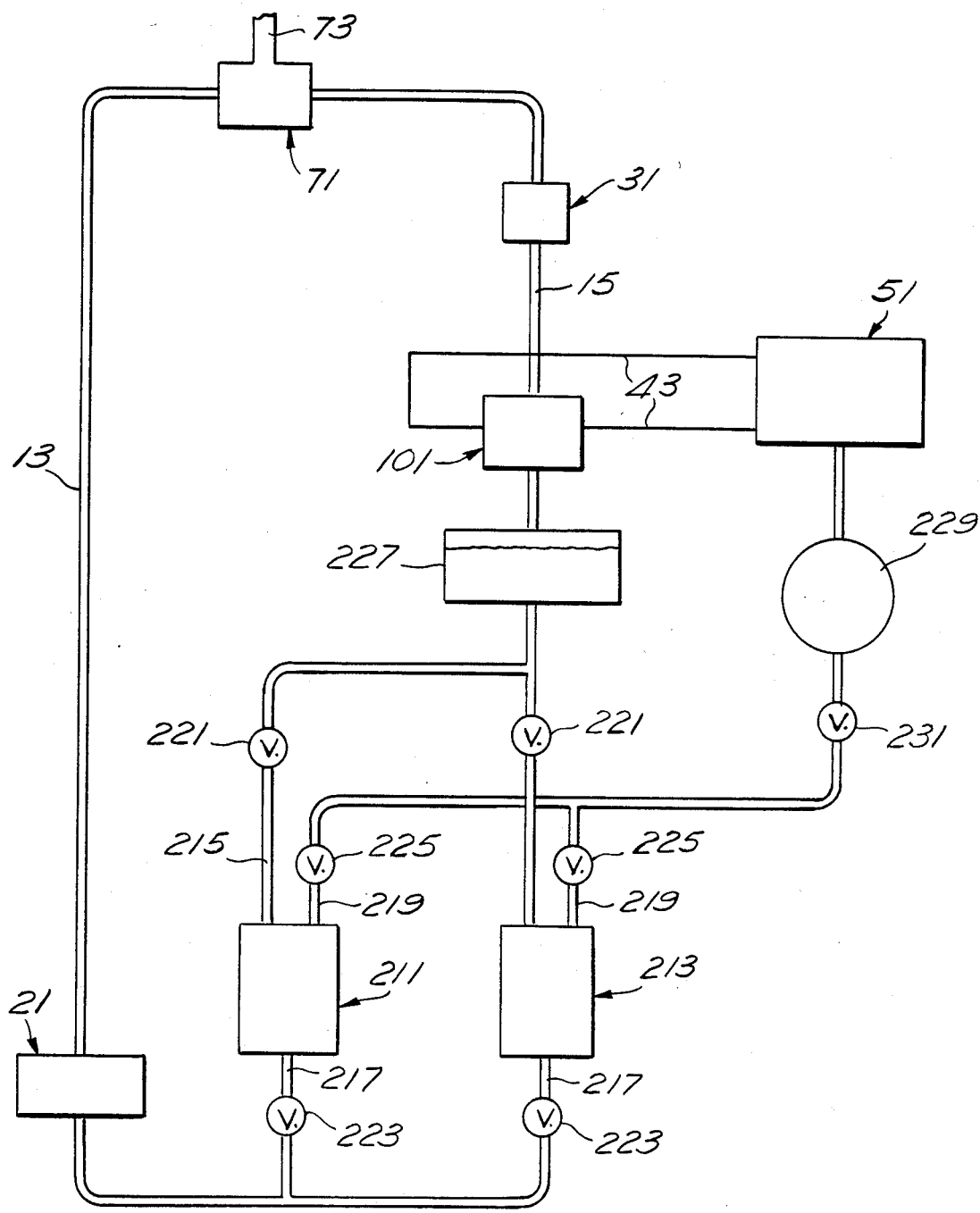
FIG. 11 is a schematic drawing of a fifth alternative embodiment of the Energy Conversion System.

Referring now to the embodiment of the system of the invention shown in FIG. 11, the overall system is again roughly the same as that described above, with a pair of flow tubes 13, 15, an electric generator 101, and a gas generator 51 that uses the electric energy generated by the electric generator 101. The gas generator 51 and the electric generator 101 are connected by the electrical leads 43. The system includes an energy input means 21, such as a thermal energy source or other means to begin the flow of fluid through the conduit, such as a pump. If the thermal energy source is used, then, as with the previously described system, the heat exchanger 31 is again necessary to remove the heat from the fluid to maintain the temperature differential between the portions of the fluid in each column.

Rather than using the gas generated by the gas generator 51 to reduce the density of fluid in the upflow column 13, however, the embodiment shown in FIG. 10 uses the gas generated by the gas generator 51 to build up pressure behind the fluid to drive the fluid through the conduit in an efficient manner.

To use the gas to propel the fluid through the conduit, a pair of fluid containers 211, 213 each has a fluid inlet 215 and fluid outlet 217, in addition to a gas inlet 219. Each of these inlets 215, 219 and outlets 217 is controlled by a valve 221, 223, 225 to control the flow of fluid into and out of the container 211, 213.

The gas from the gas generator 51 is supplied alternately to the first and second fluid containers 211, 213. Initially, the fluid inlet valve 221 on the first fluid container 211 is opened and the first container 211 is substantially filled with the system working fluid. Then the fluid inlet valve 221 is closed, and the gas inlet valve 225 is opened. The gas is supplied to the gas inlet 219 at a high pressure, so the gas builds the pressure inside the container 211. When the pressure reaches a specified level, the fluid outlet valve 223 is opened, and the pressure inside the fluid container 211 drives the fluid out of the first fluid container 211 through the upflow tube 13 and down through the downflow tube 15 and the electric energy generator 101. As the flow is driven by the pressure, it is at a higher rate than the initial flow, thus increasing the production of electric energy by the electric generator 101.

While the first fluid container 211 is being pressurized, the fluid inlet valve 221 for the second fluid container 213 is opened and the fluid is allowed to flow into the second fluid container 213 to substantially fill it. The second fluid container 213 is then pressurized in the same way as the first fluid container 211 while the fluid is being driven out of the first fluid container 211.

While the second fluid container 213 is being pressurized, the first container 211 is again filled with fluid. As the fluid is driven from the second fluid container 213, the first container 211 is again pressurized. This alternating process continues indefinitely, using the two fluid containers 211, 213 to maintain a constant flow of fluid through the conduit 13, 15.

Obviously, more than two fluid containers may also be used in a system that operates such as this to further increase the fluid flow.

To minimize the need for pumps and other expensive equipment, the fluid containers 211, 213 are fed from a reservoir 227 that is at the bottom of the downflow tube 15, and at an elevation higher than the elevation of the first and second fluid containers 211, 213. In this way, when the fluid inlet valve 221 on one of the fluid containers 211, 213 is opened, the fluid will flow into the container by gravitational force, eliminating the need for a pump or other fluid moving apparatus.

To ensure an adequate high pressure supply of gas to pressurize the first and second fluid containers 211, 213 a gas accumulator 229 is connected to the output of the gas generator 51. This accumulator 229 collects the gas generated by the gas generator 51 and allows the gas to build up to a very high pressure. It is well known that the electrolysis process of gas generation can produce gasses at very high pressures without significant loss in efficiency or overall energy consumption. Thus, the gas accumulator 229 allows the pressure of gas to be built up before it is fed through the gas inlets 219 to the first and second fluid containers 211, 213.

A gas separator 71 at the top of the upflow column 13 allows any gas that has been introduced into the working fluid by the fluid flow augmentation to be removed before the working fluid flows downward through the second column 15 and the electric generator 101.

THERMAL ENERGY CONVERSION SYSTEM COUPLED WITH FERMENTATION REACTION

Alternative embodiments of the Thermal Energy Conversion System use products from fermentation to increase the rate of the fluid flow.

The fermentation reaction, which is well known in the art, is characterized by the following molar equation

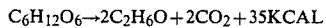

$$C_6H_{12}O_6 \rightarrow 2C_2H_6O + 2CO_2 + 35\text{KCAL}$$

This fermentation reaction uses the zymase enzyme secreted by yeast cells as a catalyst for breaking down glucose ($C_6H_{12}O_6$) molecules. Several chemically complex carbohydrates, such as grains, corn and potatoes, produce the glucose through processes which are well known in the art. The glucose is typically in solution with water.

The fermentation reaction produces ethyl or grain alcohol ($2C_2H_6O$), a product which has many well know uses. However, the fermentation reaction slows down as the amount of alcohol in the mixture increases. The fermentation reaction tends to stop when the concentration of alcohol in the solution is around 17%. Higher concentrations of alcohol can be produced by distillation, another well known process, but the distillation process requires the input of energy.

The carbon dioxide ($CO_2$) and heat (35KCAL) products of this fermentation reaction are of special importance to such embodiments of the present invention. The carbon dioxide is a gas produced through fermentation under high pressure without reducing the rate of chemical reaction. Heat is removed from the fermentation reaction to prevent the temperature of the fermentation solution from rising. For the yeast to secrete the zymase enzyme, the temperature of the yeast in the glucose solution must remain low enough to keep the yeast alive. However, the temperature of the yeast must also remain high enough to prevent the production of zymase from declining. Thus, the heat is controlled so that the temperature is kept in an optimum range for the fermentation reaction, usually within 65-70 F.

GENERAL SYSTEM COUPLED WITH FERMENTATION PROCESS

Figure 12:
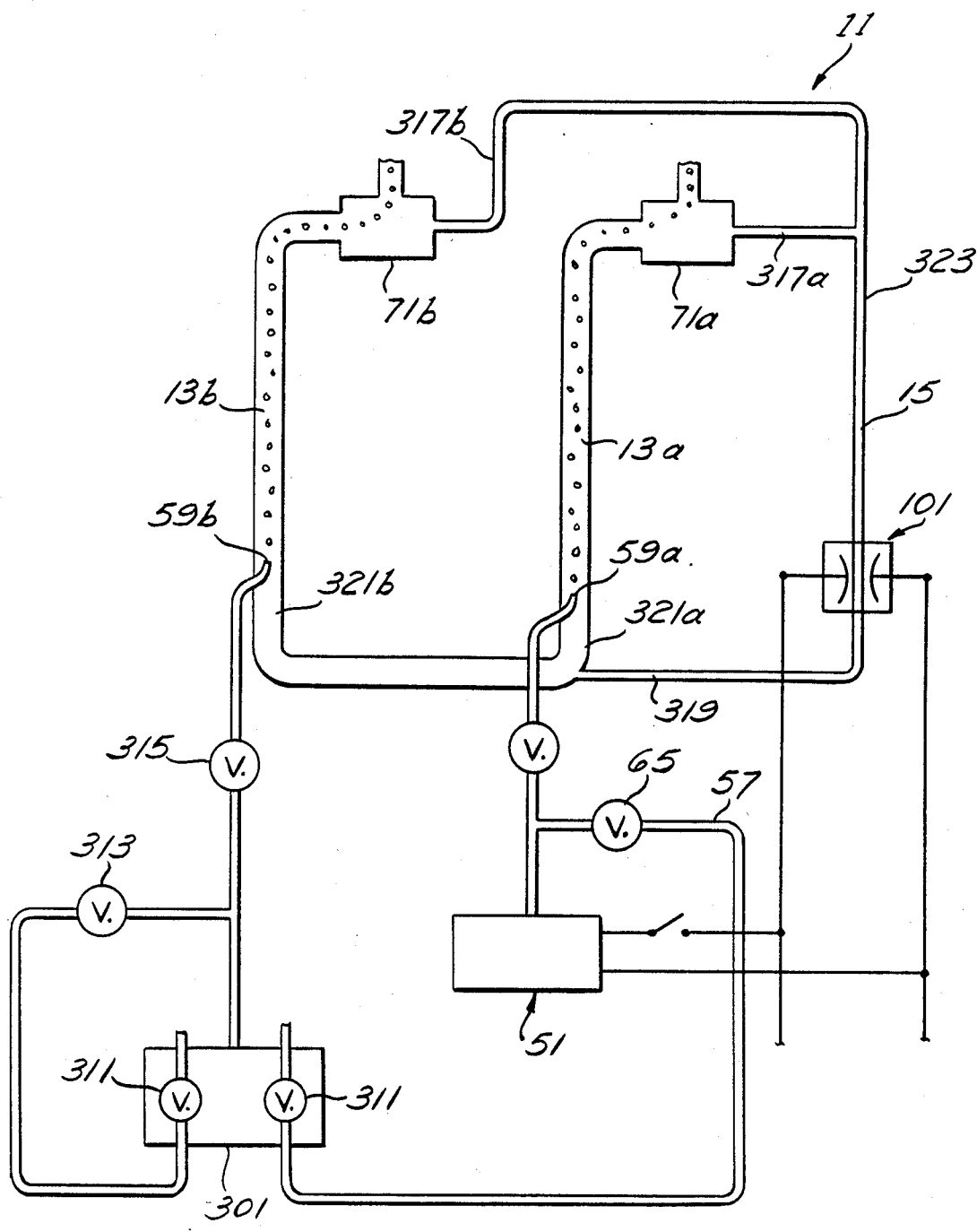
FIG. 12 is a schematic drawing of a sixth alternative embodiment of the Energy Conversion System with fermentation of the present invention.

The embodiment of the present invention shown in FIG. 12 incorporates the fermentation reaction with the general system described above in connection with FIG. 7.

The general system sections described above include fluid loop 11 comprised of columns 13a, and 13b, and 15. Columns 13a and 13b represent flow increase columns in which the rate of the flow through fluid loop 11 is increased by injecting a gas through injection nozzles 59a and 59b located therein. Flow increase columns 13a and 13b are connected to fluid return column 15 so that a fluid loop is formed. The fluid which exits from columns 13a and 13b at flow increase column fluid exit ends 317a and 317b enters column 15 at return column fluid entry end 323. This fluid is returned by leaving column 15 at return column fluid exit end 319 and entering columns 13a and 13b at flow increase column fluid entry ends 321a and 321b. Two distinct flow increase columns 13a and 13b are provided so that the gas which enters the fluid at injection nozzle 59a inside flow increase column 13a does not mix with the gas which enters the fluid at injection nozzle 59b inside flow increase column 13b. Gas separators 71a and 71b remove the gasses which were mixed with the fluid in columns 13a and 13b respectively, substantially preventing mixing of the gasses in return column 15.

Electric generator 101 converts kinetic energy of the flowing fluid into electricity. The quantity of electricity produced is proportional to the flow rate of the fluid. At least a portion of the electricity generate din electric generator 101 is used by gas generator 51 to form a quantity of gas proportional to the electricity produced and to the flow rate of the fluid. The gas forms under pressure and is fed back to the fluid in column 13a to augment the fluid flow by converting the potential energy inherent in the pressurized gas into kinetic energy of the flowing fluid. The excess electricity has a number of uses, including the distillation of the fermentation solution to increase the concentration of alcohol.

In a preferred embodiment gas generator 51 electrolyzes water to produce hydrogen and oxygen. Since a combination of these two gasses can be explosive, separating the gasses is advantageous. The embodiment of FIG. 12 contemplates the use of only one of these gasses at injection nozzle 59a thereby preventing any explosive situation from occurring. However, the other of the gasses can also augment the fluid flow by the addition of a third flow increase column and gas separator (not shown).

The fermentation reaction occurs in fermentation vat 301. Fermentation vat 301 contains the glucose and yeast solution and is sealed so that its contents are maintained under pressure. Since fermentation vat 301 is sealed, the carbon dioxide gas given off in the fermentation chemical reaction builds up pressure as the reaction progresses. As is known in the art, pressure greater than 450 psi is obtained in this manner without substantially affecting the fermentation reaction.

The carbon dioxide gas produced in fermentation vat 301 under pressure also causes the fluid in fluid loop 11 to flow. Since the gas is under pressure, it does work against the fluid, thereby converting the potential energy inherent in the pressure of the gas into kinetic energy of the fluid. A value 315 keeps the fluid in the fluid loop 11 out of the fermentation vat 301 by remaining closed until the pressure in fermentation vat 301 is sufficient to force the carbon dioxide to enter the fluid through injection nozzle 59b. Valve 313 adjusts the proportion of carbon dioxide gas between the amount which enters the fluid and the amount used for other purposes.

The embodiment of FIG. 12 shows the carbon dioxide from the fermentation vat 301 as the primary propellant of the fluid in fluid loop 11. In this embodiment the fluid remains stationary until the fermentation reaction in the fermentation vat 301 builds up sufficient pressure to open the valve 315. When the valve 315 opens, the pressure forces the carbon dioxide through injection nozzle 59b and into the fluid. The fluid then tends to flow for a combination of several reasons. The force of the carbon dioxide gas as it is impelled into the fluid through injection nozzle 59b working against the attractive forces of the fluid molecules provides one cause of fluid flow. The carbon dioxide is injected under relatively high pressure, but expands to a lower pressure after injection. The expansion of the gas additionally tends to cause the fluid to flow. Finally, if flow increase column 13b is substantially vertical a buoyancy effect tends to cause the fluid to flow.

After the fluid is flowing due to the injection of carbon dioxide gas, the gas or gasses formed in the gas generator 51 provide a secondary propellant. The secondary propellant increases the system efficiency by utilizing the pressure inherent in a pressurized gas that would not otherwise be used. The secondary propellant begins to augment the flow rate after the fluid begins to flow.

The pressurized fermentation and generated gasses are additionally used to refrigerate the fermentation reaction in embodiments constructed in milder climates. The fermentation reaction releases heat energy which must be removed from the glucose solution to prevent the solution's temperature from rising. The gasses, which are under pressure, expand through expansion valves 311 to a lower pressure, thereby producing a refrigeration effect well known in the art. The expanding gasses absorb the unwanted heat energy and then exit fermentation vat 301 taking the heat with them. Valves 313 and 65 control the amount of gasses expanded and therefore the amount of refrigeration. With an adequate temperature differential, this fermentation reaction heat may advantageously be used as the heat source 21, possibly with no refrigeration effect being necessary.

FERMENTATION REACTION COUPLED WITH FIRST ALTERNATIVE FLOW AUGMENTATION MEANS

Figure 13:
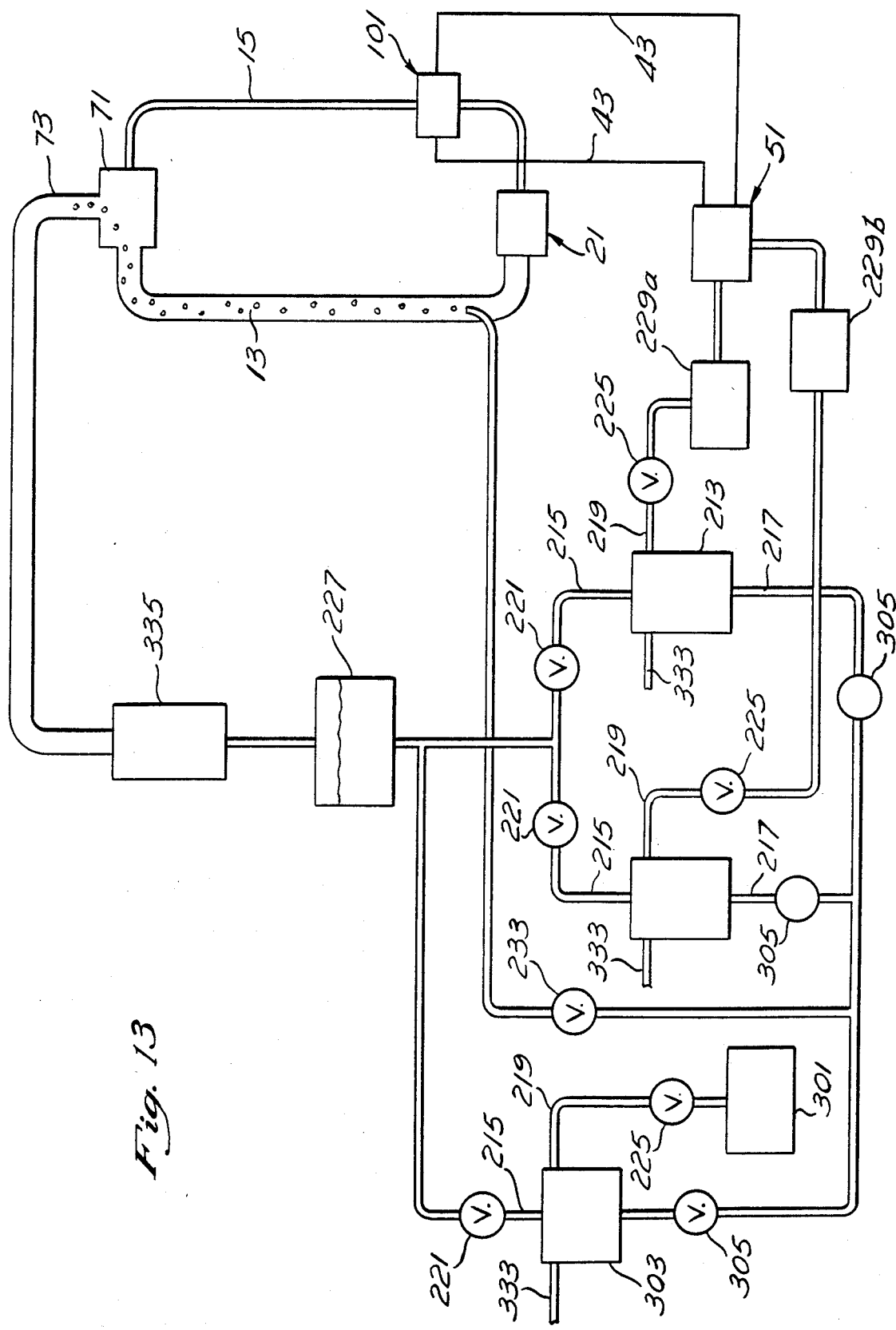
FIG. 13 is a schematic drawing of a seventh alternative embodiment of the Energy Conversion System with fermentation of the present invention.

Referring to the embodiment of the invention shown in FIG. 13, the overall system roughly shows the first alternative flow augmentation means described above in connection with FIG. 10 incorporating the fermentation process. The carbon dioxide produced in the fermentation vat 301 is under pressure, as is the generated gas in gas accumulators 229. Likewise, the carbon dioxide gas is used to propel the volatile fluid in a manner similar to the propulsion from the generated gas from gas accumulators 229. However, instead of the mere alternating process described above in conjunction with the first alternative flow augmentation means, the volatile fluid generated in the embodiment of FIG. 13 origi- nates from any of the chambers 211, 213, 303, depending on which chamber is under the greatest pressure. One of the valves 305 opens to propel the volatile fluid.

FIG. 13 shows an embodiment of the system in which the heat added to the fluid at the thermal source 21 is absorbed by the volatile fluid as the volatile fluid changes state from a liquid to a gas. The heat is then removed as the gas exits from the fluid loop in gas separator 71. An additional heat exchanger is not necessary in this embodiment because heat is removed with the volatile fluid. The volatile fluid is converted to a gas as it is injected into the flow at injection nozzle 59 and is separated from the fluid in gas separator 71. The volatile fluid then enters condenser 335 in the gaseous state from gas separator 71 and exits condenser 335 in the liquid state to be recycled to reservoir 227.

Gas venting means 333 allows the gas in chambers 303, 211, and 213 to be vented out of the chamber after the volatile fluid has been injected through nozzle 59. When the gas has been evacuated from the respective chamber, the appropriate valve 221 may be opened to let additional volatile fluid enter the chamber. The gas vented from the respective chamber at a venting means 333 may advantageously be put to several uses. Such gasses may advantageously be further expanded to refrigerate the glucose solution in the fermentation vat 301. Additionally, the gasses may advantageously be added to the fluid in the upflow column 13 to further augment the fluid flow.

The gas accumulators 229 consist of two individual accumulators, 229a and 229b. The individual accumulators aid in keeping different gaseous elements apart. In the preferred embodiment water is electrolyzed in the gas generator 51 to form the two gaseous elements of hydrogen and oxygen. The gas accumulator 229a pressurizes one of these two element gasses before the element gas is fed to the chamber 213 through a valve 225 and a gas inlet 219. Likewise, the second gas accumulator 229b pressurizes the other of the two gases before the element gas is fed to the chamber 211 through a similar valve 225 and a gas inlet 219. The gas chambers 211, 213 each have their own gas venting means 333 to continue the separation of the hydrogen and oxygen gasses.

FERMENTATION REACTION COUPLED WITH SECOND ALTERNATIVE FLOW AUGMENTATION MEANS

Figure 14:
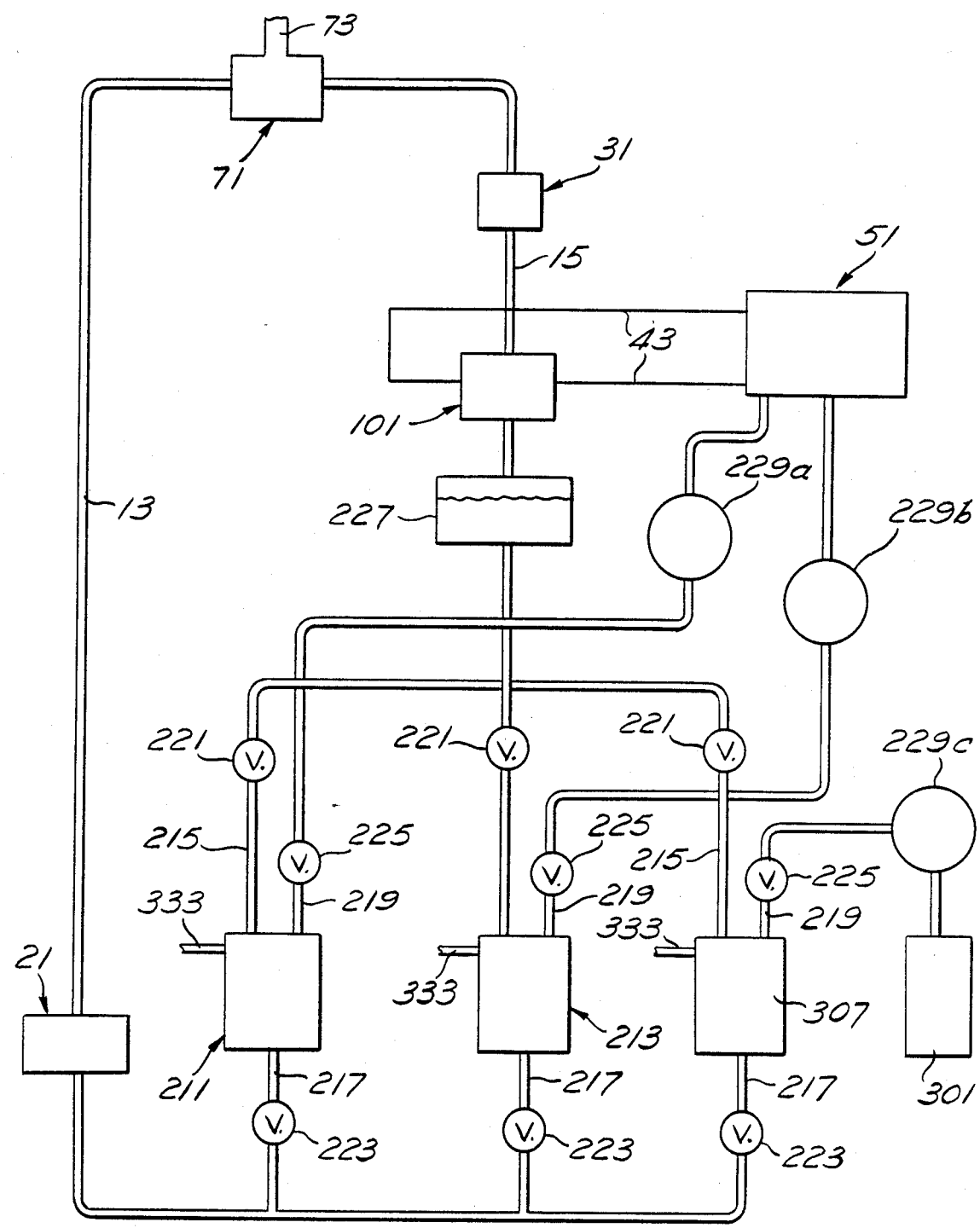
FIG. 14 is a schematic drawing of a seventh alternative embodiment of the Energy Conversion System with fermentation of the present invention.

Referring to the embodiment of the invention shown in FIG. 14, the overall system roughly shows the above described second alternative flow augmentation means incorporating the fermentation process. The system again contains flow tubes 13, 15, an electric generator 101, and a gas generator 51. The gas formed in the gas generator 51 is pressurized in gas accumulators 229a, 229b and injected into fluid containers 211, 213, respectively. Additionally, the containers 211, 213 are coupled to a reservoir 227 for receiving fluid flowing in fluid return column 15. The gas in the chambers 211, 213 pressurizes and forces this fluid out of the chamber when a valve 223 is opened. Energy input means 21 in combination with heat exchanger 31 additionally causes the fluid to flow as described in embodiments mentioned above.

Carbon dioxide gas forms in a fermentation vat 301. This gas is under pressure, as is the gas in the gas accumulators 229a, 229b. Likewise, the carbon dioxide gas is used to propel the conducting fluid, as the generated gas in the gas accumulators 229a, 229b is also used. The carbon dioxide gas liberated in the fermentation reaction is collected and pressurized in a gas accumulator 229c, and fed to a container 307 when a valve 225 is opened in a manner similar to that described above for the gas formed in gas generator 51. The container 307 additionally receives fluid from reservoir 227 through a valve 221 and a fluid inlet 215. Further, in a manner similar to that described above, the fluid is forced out of the container 307 through a valve 223 by the pressure exerted from the pressurized carbon dioxide gas.

Figure 15:
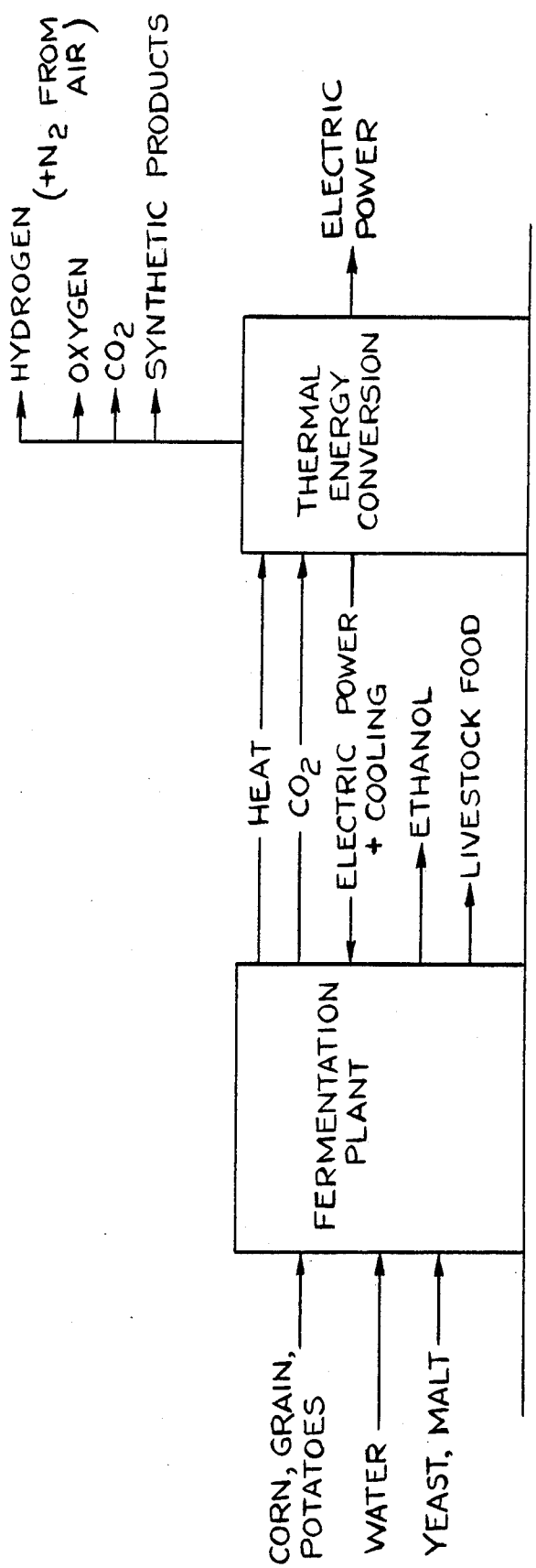
FIG. 15 is a schematic view indicating the energy transfer in the systems of FIGS. 12-14.

The embodiment of the present invention shown in FIG. 15 includes a system for keeping three gaseous fluids separated. The two gas sources produce three gaseous fluids. The gas generator 51 advantageously electrolyzes water into the two gasses hydrogen and oxygen. The fermentation reaction conducted in the fermentation vat 301 forms carbon dioxide as the third gas. These three gasses each have an individual gas accumulator 229a, 229b, 229c. They each have respective individual containers 211, 213, 307. Likewise, they have individual gas venting means 333. The three gasses are substantially kept apart from each other, thus preventing further reactions between these gasses, which may be explosive or otherwise detract from the overall operation of the system. Trace amounts of gas mixed with the fluid are removed in gas separator 71 thereby preventing any buildup of gasses in the fluid.

It should be noted that the gasses available at the venting means 333 are very useful. In particular, electrolytically produced elements are extremely pure (called nascent or newborn) and are invaluable for certain chemical processes.

For example, in the Haber process for synthesizing ammonia, atmospheric nitrogen reacts with pure hydrogen at 200° C. and 30 atmospheres to give a 68% yield of $NH_3$. The ammonia gas under pressure can also be used as a refrigerant, but the process itself produces 2400 calories per Mol, and this heat can be used to further accelerate the gas flow in the tube 13.

Also, the ammonia can be combined with the pure oxygen produced to synthesize nitric acid (Ostwald process) forming the basis of an entire spectrum of products. Clearly, the hydrogen together with $CO_2$ forms the basis for many hydrocarbons, such as methane, methyl alcohol, acetylene, and so on.

A numerical example of quantities involved in the fermentation process may be useful to appreciate the invention. Two hundred twenty pounds of potatoes contains approximately 20% starch, equalling 44 pounds of starch, which, when converted to glucose and fermented, yields 12 liters of 95% ethanol, 4.6 cubic meters of $CO_2$, 150 liters of swill, plus heat.

In a small fermentation plant employing around 80,000 gallons of fermenting liquids, 12,000 gallons of ethanol per day plus 609,000 cubic feet of $CO_2$ and 16,000 KWH of heat energy are produced. This amount of heat energy and $CO_2$ production is more than enough to run a 225 KW thermal conversion plant, which not only provides the needed electrical power for the fermentation and distillation, but will also produce 50,000 cubic feet of hydrogen per day.

Thus, it can be seen that the combined thermal conversion and fermentation processes working together provide each other with the needed energy to perform vital functions that are often supplied today with the consumption of fossil fuel and nuclear power. Much of the energy from the fermentation processes can be provided from surplus materials that are frequently disposed of for less useful purposes. In short, these two processes working together utilize the solar energy stored in natural carbohydrate products and converts them into hydrocarbon fuels, electrical power and numerous other invaluable byproducts. FIG. 15 schematically illustrates the energy flow and transformation, as well as the byproducts available through the processes disclosed.

I claim:

1. An apparatus for converting thermal energy into an alternate form of energy, comprising:
   (1) a fluid loop through which flows a liquid, said loop comprising:
      (a) at least one flow increase column having fluid entry and fluid exit ends;
      (b) a fluid return column having a fluid entry and a fluid exit end;
      (c) interconnection means between the fluid exit end of said flow increase columns and the fluid entry end of said fluid return column; and
      (d) interconnection means between the fluid entry ends of said flow increase columns and the fluid exit end of said fluid return column;
   (2) means for producing carbon dioxide gas from fermentation.
   (3) means for causing said liquid to flow through said loop by introducing a portion of said carbon dioxide gas into one of said flow increase columns;
   (4) electrical generator means for generating electrical energy from said flowing liquid, the amount of electrical energy generated being proportional to the velocity of the flow of said liquid; and
   (5) means for supplementing said flow to increase the electrical energy generated by said electrical generator means comprising:
      (a) an electrolytic gas generator coupled to said electrical generator means for using at least a portion of said electrical energy to electrolyze a second liquid to form a gas, said gas containing chemical energy; and
      (b) means for introducing a portion of said gas into one of said flow increase columns so that expansion of said electrolyzed gas causes said flow to increase.

2. An apparatus for converting one form of energy into an alternate form of energy, comprising:
   (1) a fluid conduit through which flows a first fluid;
   (2) a fermentation vat wherein fermentation is conducted to produce a gas, said gas under pressure;
   (3) first means, coupled to said fermentation vat, for establishing a flow of said first fluid through said conduit by using said pressurized fermentation gas;
   (4) second means coupled to said conduit for generating electrical energy from said flowing fluid, the amount of electrical energy generated being proportional to the velocity of the flow of said fluid;
   (5) third means coupled to said second means for using at least a portion of said electrical energy to form a gas; and
   (6) a fluid container having an outlet coupled to said fluid conduit, wherein:
      (a) said container is adapted to receive a second fluid; and
      (b) said container is additionally coupled to said third means so that said gas formed by said third means pressurizes said second fluid in said container so that when said outlet is opened said second fluid is propelled out of said container into said conduit to increase the rate of flow of said first fluid through said conduit.

3. The apparatus defined in claim 2, additionally comprising a second fluid container, substantially identical to said first fluid container, and additionally coupled to said fluid conduit so that said second fluid may be alternately propelled from said first fluid container and from said second fluid container.

4. An apparatus for converting one form of energy into an alternate form of energy, comprising:
   (1) a fluid conduit through which flows a fluid;
   (2) first means for establishing a flow of said fluid through said conduit;
   (3) second means coupled to said conduit for generating electrical energy from said flowing fluid, the amount of electrical energy generated being proportional to the velocity of the flow of said fluid;
   (4) third means coupled to said second means for using at least a portion of said electrical energy to form a gas;
   (5) a first fluid container having a first container outlet coupled to said fluid conduit, wherein said fluid container is additionally coupled to said third means so that said gas formed by said third means pressurizes the fluid in said first container so that when said first container outlet is opened, said fluid is propelled out of said first container through said fluid conduit;
   (6) a fermentation vat wherein a gas is produced under pressure by a fermentation reaction;
   (7) a second fluid container, having a second container outlet coupled to said fluid conduit, and additionally having an inlet coupled to said fermentation vat, so that said fermentation gas pressurizes the fluid in said second container so that when said second container outlet is opened, said fluid is propelled out of said second container through said fluid conduit.

5. The apparatus defined in claim 4, additionally comprising a third fluid container, substantially identical to said first fluid container, and additionally coupled to said fluid conduit and said third means so that fluid may be separately propelled from said first fluid container and from said third fluid container into said conduit.

6. An apparatus for converting one form of energy into an alternate form of energy, comprising:
   (1) a fluid conduit through which flows a fluid;
   (2) first means for establishing a flow of said fluid through said conduit;
   (3) second means for collecting a first gas under pressure;
   (4) third means for using at least a portion of said first gas to increase the rate of flow of said fluid through said conduit, wherein said third means comprises a first container having a first container outlet that can be selectively opened and closed, wherein said first container is coupled to said second means so that a portion of said first gas pressurizes a second fluid in said first container so that when said first container outlet is opened, said second fluid is propelled out of said first container into said fluid conduit to increase the rate of flow of said first fluid in said conduit;
   (5) fourth means coupled to said conduit for generating electrical energy from said flowing fluid;
   (6) fifth means coupled to said fourth means for using at least a portion of said electrical energy to form a second gas; and
   (7) sixth means for using at least a portion of said second gas to increase the rate of flow of said fluid through said fluid conduit, wherein said sixth means comprises a second fluid container having a second container outlet that can be selectively opened and closed, wherein said second container is coupled to said fifth means so that a portion of said second gas pressurizes a second fluid in said second container so that when said second container outlet is opened, said second fluid is propelled out of said second container into said fluid conduit to increase the rate of flow of said first fluid in said conduit.

7. The apparatus defined in claim 6, additionally comprising means for removing said second fluid from said conduit.

8. The apparatus defined in claim 6, wherein said sixth means additionally comprises a second gas accumulator having an inlet coupled to said fifth means and an outlet coupled to said second container so that said second gas accumulator:
   (1) receives said second gas from said fifth means;
   (2) stores said second gas at a pressure; and
   (3) supplies said second gas under pressure to said second container.

9. The apparatus defined in claim 6, additionally comprising a fluid source coupled to said first and second containers to supply said containers with said second fluid.

10. The apparatus defined in claim 9, wherein:
   (1) said second fluid is a volatile liquid; and
   (2) said fluid source is a reservoir located at a higher elevation than said fluid container so that said second fluid flows into said fluid container and said chamber due to gravitational force.

11. An apparatus for converting one form of energy into an alternate form of energy, comprising:
   (1) a fluid conduit through which flows a fluid;
   (2) first means for estabishing a flow of said fluid through said conduit;
   (3) second means for collecting a first gas under pressure;
   (4) third means for using at least a portion of said first gas to increase the rate of flow of said fluid through said conduit, wherein said third means comprises a first container having a first container outlet that can be selectively opened and closed, wherein said first container is coupled to said second means so that a portion of said first gas pressurizes said fluid in said first container so that said fluid is propelled out of said first container into said fluid conduit to increase the rate of flow of said fluid in said conduit;
   (5) fourth means coupled to said conduit for generating electrical energy from said flowing fluid;
   (6) fifth means coupled to said fourth means for using at least a portion of said electrical energy to form a second gas; and
   (7) sixth means for using at least a portion of said second gas to increase the rate of flow of said fluid through said fluid conduit, wherein said sixth means comprises a second container having a second container outlet that can be selectively opened and closed, wherein said second container is coupled to said fifth means so that a portion of said second gas pressurizes said fluid in said second container so that said fluid is propelled out of said second container into said fluid conduit to increase the rate of flow of said fluid in said conduit.

12. An apparatus for converting one form of energy into an alternate form of energy, comprising:
 (1) a fluid conduit through which flows a fluid;
 (2) a fermentation vat wherein a yeast fermentation process is conducted to produce a gas under pressure;
 (3) means coupled to said fermentation vat, for establishing a flow of said fluid through said conduit by using said pressurized fermentation gas; and
 (4) means coupled to said conduit for generating electrical energy from said flowing fluid.

13. The apparatus of claim 12 including means for injecting said gas into the fluid to increase the fluid flow rate.

14. An apparatus for converting one form of energy into an alternate form of energy, comprising:
 (1) a fluid conduit through which flows a fluid;
 (2) a fermentation vat wherein fermentation is conducted to produce a gas under pressure;
 (3) means coupled to said fermentation vat, for establishing a flow of said fluid through said conduit by using said pressurized fermentation gas;
 (4) means coupled to said conduit for generating electrical energy from said flowing fluid; and
 (5) means for injecting said gas into the fluid to increase the fluid flow rate;
 (6) wherein the heat of fermentation is used to heat the fluid to increase the fluid flow rate.

15. The apparatus of claim 12 including means coupled to said generating means for using at least a portion of said electrical energy to form a gas which is used to increase the rate of flow through said conduit.

16. A method for converting one form of energy into an alternate form of energy, comprising:
 (1) producing a gas under pressure by fermentation;
 (2) establishing a flow of a second fluid through a fluid conduit by using said pressurized fermentation gas; and
 (3) generating electrical energy from said flowing second fluid, the amount of electrical energy generated being proportional to the velocity of the flow of said second fluid.

17. A method for converting one form of energy into an alternate form of energy, comprising:
 (1) producing a gas under pressure by fermentation;
 (2) establishing a flow of fluid through a fluid conduit by using said pressurized fermentation gas;
 (3) generating electrical energy from said flowing fluid, the amount of electrical energy generated being proportional to the velocity of the flow of said fluid; and
 (4) utilizing the heat of fermentation to heat said fluid.

18. The method of claim 17 including utilizing the pressurized gas by introducing it into said fluid.

19. The method of claim 17 including utilizing the pressurized gas by propelling a second fluid into the fluid in the conduit.

20. A method for converting one form of energy into an alternate form of energy, comprising:
 (1) establishing a flow of fluid through a conduit;
 (2) collecting a first gas under pressure;
 (3) using a portion of said gasses to pressurize a second fluid, wherein said second fluid is pressurized in a first container by the first gas and in a second fluid container by the first gas so that the containers can be selectively opened and closed to propel said second fluid out of said first and second containers into said fluid conduit to increase the rate of flow of said first fluid in said conduit; and
 (4) generating electrical energy from said flowing fluid.

21. The method of claim 20 comprising removing said second fluid from said conduit.

22. The method of claim 20 including accumulating a quantity of said second gas and supplying it under pressure to said second container.

23. A method for converting one form of energy into an alternate form of energy, comprising:
 (1) establishing a flow of fluid through a conduit by adding thermal energy to said fluid;
 (2) collecting a first gas under pressure, wherein said first gas is produced by fermentation and the heat from the fermentation process provides thermal energy to said fluid;
 (3) using at least a portion of said gas to increase the rate of flow of said fluid through said conduit;
 (4) generating electrical energy from said flowing fluid;
 (5) using at least a portion of said electrical energy to form a second gas; and
 (6) using at least a portion of said second gas to increase the rate of flow of said fluid through said fluid conduit.

24. The method of claim 16 including utilizing the pressurized gas by introducing it into said second fluid.

25. The method of claim 16 including utilizing the pressurized gas by propelling a third fluid into said second fluid flowing in a conduit.

26. An apparatus for converting one form of energy into an alternate form of energy, comprising:
 (1) a fluid conduit through which flows a fluid;
 (2) a fermentation vessel wherein a yeast fermentation process is conducted to produce heat;
 (3) means coupling said fermentation vessel and said fluid conduit to transfer the heat produced by said fermentation process to the fluid in said fluid conduit to promote said fluid flow through said conduit; and
 (4) a generator for generating electrical energy from said flowing fluid.

27. The apparatus defined in claim 26, wherein said fermentation process additionally produces $CO_2$ gas under pressure in said fermentation vessel, and said apparatus additionally comprises an injector for using at least a portion of said pressurized $CO_2$ to increase the rate of flow of said fluid.

28. The apparatus defined in claim 27, wherein said injector injects at least a portion of said pressurized $CO_2$ into said fluid conduit to increase the rate of flow of said fluid.

29. The method of claim 23 including utilizing refrigeration means connected to said first and second gasses and using at least a portion of said gasses to remove a portion of said heat energy from said fermentation.

* * * * *